United States Patent [19]

Bühler et al.

[11] 4,304,919

[45] Dec. 8, 1981

[54] PROCESS FOR THE PRODUCTION OF ASYMMETRICAL THIOINDIGO COMPOUNDS

[75] Inventors: Niklaus Bühler, Rheinfelden; Hans Bosshard, Basel, both of Switzerland

[73] Assignee: Ciba-Geigy Corporation, Ardsley, N.Y.

[21] Appl. No.: 167,887

[22] Filed: Jul. 14, 1980

[30] Foreign Application Priority Data

Jul. 18, 1979 [CH] Switzerland .................... 6682/79

[51] Int. Cl.³ .......................................... C07D 333/64
[52] U.S. Cl. ...................................... 549/52; 549/45; 549/54; 549/55; 549/56
[58] Field of Search ............... 549/45, 52, 54, 55, 549/56

[56] References Cited

U.S. PATENT DOCUMENTS

| | | | |
|---|---|---|---|
| 2,882,277 | 4/1959 | Mueller et al. | 549/54 |
| 3,793,341 | 2/1974 | Genta | 549/54 X |
| 3,960,479 | 6/1976 | Tsujinoto et al. | 549/54 X |
| 3,963,429 | 6/1976 | Tsujinoto et al. | 549/52 X |
| 4,154,739 | 5/1979 | Buhler et al. | 549/45 |

FOREIGN PATENT DOCUMENTS 2401981 8/1974 Fed. Rep. of Germany .
2804842 8/1978 Fed. Rep. of Germany .

OTHER PUBLICATIONS

Rodd, et al., Chemistry of Carbon Compounds, vol. IV, part B, (1977), pp. 358–360.
Olah, Friedel–Crafts and Related Reactions, vol. III, (1965), pp. 578–581.
Houben–Weyl, vol. 7, No. 4, p. 39 (1968).
Fiat, 1313, II, p. 297, Feb. 1, 1948.

*Primary Examiner*—Joseph P. Brust

*Attorney, Agent, or Firm*—John P. Spitals; Edward McC. Roberts

[57] ABSTRACT

The invention relates to asymmetrical thioindigo compounds of the formula I

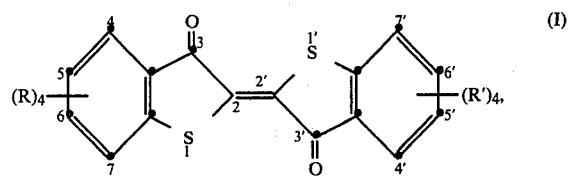

wherein at least one substituent R is different from a substituent R' and preferably at most three Rs or R's are different from hydrogen, e.g. the compound (I), wherein theRs and R's in the positions 4, 6, 7, 4', 6' and 7' are hydrogen, the R in position 5 is methyl and the R' in position 5' is —($CH_2$)-$OCOCH_3$. These compounds can be obtained by a novel process in simple and economic manner and in high purity by reacting a compound of the formula II

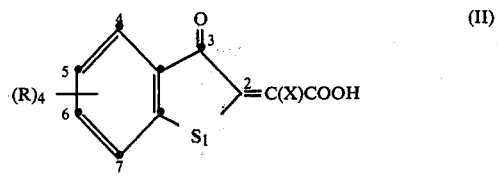

(wherein X is halogen) with corresponding thiophenols, and cyclising the unsubstituted or substituted 2-thiophenyl-carboxymethylene-benzothiophen-3-ones thereby obtained. Some of the compounds of the formula I are known per se and they are used, inter alia, as disperse, melt spinning and pigment dyes.

9 Claims, No Drawings

PROCESS FOR THE PRODUCTION OF ASYMMETRICAL THIOINDIGO COMPOUNDS

The present invention relates to a novel process for the production of asymmetrical thioindigo compounds. The thioindigo compounds obtained by the process of the invention are used, inter alia, as vat, disperse, melt spinning and pigment dyes. Compared with corresponding symmetrical compounds, asymmetrical thioindigo compounds are distinguished in general by lower melting points, better solubility in organic solvents, a higher coefficient of molecular absorption, greater colour strength and brilliance, and they are suitable in particular for colouring polyester material [cf. German Offenlegungsschrift No. 2 401 981].

Asymmetrical thioindigo compounds can be obtained by different methods, e.g. by oxidative condensation of two differently substituted thianaphthen-3-ones or their carboxylic acids, or by oxidative condensation of thianaphthen-3-ones with thianaphthenequinone or 2,2-dibromo-thianaphthen-3-ones. These methods, however, yield mixtures of symmetrical and asymmetrical thioindigo compounds which can only be separated with difficulty. In a further process, thiosalicylic acids are reacted with 1,2-dichloroethylene and the reaction product is dehydrated with chlorosulfonic acid to give the thioindigo compound [cf. for example Rodd's Chemistry of Carbon Compounds, Vol IV, Part B, 359–360 (1977)]. On account of the low yield and the somewhat hazardous method of obtaining substituted thiosalicylic acids (reaction of diazotised substituted anthranilic acids with thiol compounds), this latter process has achieved only very limited economic importance. The most important method of obtaining asymmetrical thioindigo compounds is the anil process, i.e. the oxidative condensation of thianaphthen-3-one with an anil of a thianaphthenone, e.g. 2-(4'-dimethylaminophenylimino)-thianaphthen-3-one. The process to obtain the anil from the thianaphthenones by reaction with suitable nitroso compounds also results in the formation of symmetrical thioindigo compounds as by-products. In addition, reactions with nitroso compounds are undesirable for environmental reasons [cf. Houben-Weyl, 7/4, page 39].

The thianaphthen-3-ones are obtained in turn by cyclisation of phenylthioglycolic acids in the presence of sulfuric acid or chlorosulfonic acid, or by conversion of the phenylthioglycolic acids into the corresponding acid chlorides and cyclisation of the acid chlorides using a Friedel-Crafts catalyst. In this process, it is necessary to take special steps to prevent a partial premature oxidation of the thianaphthenone obtained and thus to prevent the formation of substantial amounts of symmetrical thioindigo compounds [cf. for example FIAT, 1313, II, 297]. These prior art methods are not suitable or are of only limited suitability for large-scale production.

There has now been found a simple and economic process by means of which it is possible to produce asymmetrical thioindigo compounds in great purity, in good yield, and also under more favourable environmental conditions.

Accordingly, the present invention provides a process for the production of compounds of the formula I

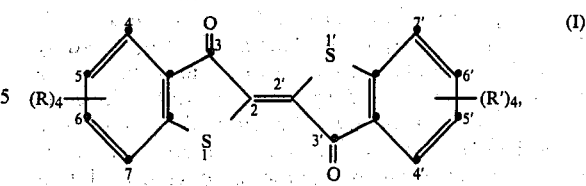

wherein two substituents R or R' are hydrogen or alkyl of 1 to 12 carbon atoms, one R or R' is hydrogen, a halogen atom or alkyl of 1 to 12 carbon atoms, and one R or R' is hydrogen, a halogen atom, alkyl, alkoxy, alkylthio, alkoxyalkyl, alkanoyloxyalkyl or alkylcarbamoyl, each containing 1 to 12 carbon atoms in the alkyl and alkoxy moieties and 2 to 13 carbon atoms in the alkanoyl moieties, or two adjacent substituents R or R' together are trimethylene or tetramethylene and the other substituents R are hydrogen, with the proviso that at least one substituent R is different from a substituent R', which process comprises reacting a compound of the formula II

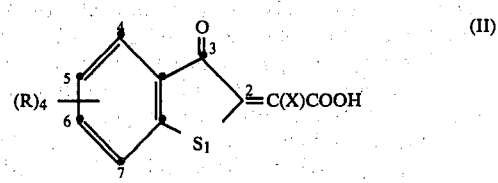

with a compound of the formula III

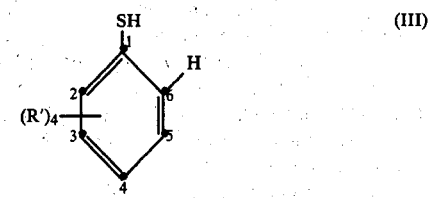

to give a compound of the formula IV

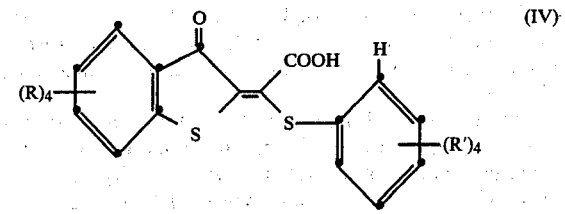

cyclising said compound of the formula IV either direct by splitting off water, preferably in the presence of a condensation agent, to give a compound of the formula I, or converting said compound of the formula IV into the corresponding acid chloride and cyclising this latter, in the presence of a Friedel-Crafts catalyst, to give a compound to the formula I, in which formulae II, III and IV above X is chlorine, bromine or fluorine and R and R' are as defined for formula I.

It is surprising that, in contrast to the processes of the prior art, the compounds of the formula I can be synthesised by introducing the central double bond not in the final stage of the synthesis by oxidative condensation of two thianaphthenone moieties, but in the initial stage, and subsequently forming the two heterocyclic rings by cyclisation. It is also surprising that the cyclisation of the compounds of the formula I does not result in the formation of a spiro-3,3-benzthien-3'-on-yl-2,3-dihydroxybenzothiophene-2-carboxylic acid with elimination of the double bond, as, according to the literature, benzoylacrylic acids always react at the double bond with the elimination of water and do not result in ring closure with participation of the carboxyl group [cf. for example G. A. Olah: Friedel-Crafts and Related Reactions, Vol. III, 1, 579–81, New york 1963–65].

The compounds of the formula I are obtained almost exclusively in the trans-form. The intermediates of the formula IV are usually cis/trans-mixtures. The intermediates of the formula IV are new and likewise constitute an object of the invention.

Alkyl, alkoxy, alkylthio, alkoxyalkyl, alkanoyloxyalkyl or alkylcarbamoyl groups represented by R or R' can be straight-chain or branched, but are preferably straightchain. Alkyl and alkoxy groups R and R' as well as alkyl and alkoxy moieties of substituents R and R' preferably contain 1 to 8, especially 1 to 4, carbon atoms, whilst alkanoyl moieties preferably contain 2 to 9, most preferably 2 to 5, carbon atoms. Representative examples of alkyl, alkoxy, alkylthio, alkoxyalkyl, alkanoyloxyalkyl or alkylcarbamoyl groups R or R' are: methyl, ethyl, n-propyl, isopropyl, n-butyl, sec-butyl, n-pentyl, n-hexyl, n-heptyl, 3-heptyl, n-octyl, n-decyl, n-dodecyl; methoxy, ethoxy, n-propoxy, n-butoxy, n-hexyloxy, n-octyloxy and n-dodecyloxy; methylthio, ethylthio, n-propylthio, isopropylthio, n-butylthio, n-pentylthio, n-hexylthio, n-heptylthio, n-decylthio; methoxymethyl, 2-methoxyethyl, 2- or 3-methoxypropyl, 3-ethoxypropyl, 2-ethoxyethyl, 2-n-propoxyethyl, 2-n-butoxyethyl, 2-sec-butoxyethyl, 4-methoxybutyl, 4-ethoxybutyl, 2-octyloxyethyl; acetyloxymethyl, 2-acetyloxyethyl, 2-propionyloxyethyl, 2-butyroxyethyl; methylcarbamoyl, ethylcarbamoyl, n-propylcarbamoyl, isobutylcarbamoyl, n-butylcarbamoyl, n-hexylcarbamoyl, n-octylcarbamoyl, n-nonylcarbamoyl and n-dodecylcarbamoyl.

Alkoxyalkyl or alkanoyloxyalkyl groups represented by R or R' are in particular —(CH$_2$)$_2$—O—alkyl or —(CH$_2$)$_2$—O— C-alkyl groups, each containing 1 to 4 carbon atoms in the alkyl moieties.

Halogen atoms X, R or R' are e.g. fluorine, chlorine or bromine. X is preferably chlorine, whilst preferred halogen atoms R or R' are bromine and, in particular, chlorine.

In the process of the present invention it is preferred to employ as compounds of the formulae II and/or III those in which two substituents R or R' are hydrogen or alkyl of 1 to 4 carbon atoms, one R or R' is hydrogen, chlorine, bromine or alkyl of 1 to 4 carbon atoms, and one R or R' is hydrogen, chlorine, bromine, alkyl, alkoxy, alkylthio, —(CH$_2$)$_2$—O-alkyl,

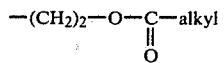

or —NHCO-alkyl, each containing 1 to 4 carbon atoms in the alkyl moieties, and X is chlorine.

If two adjacent substituents R or R' in formula II or III represent trimethylene or tetramethylene, then preferably the substituents R or R' in the 5,6- or 3,4-position have the meanings assigned to them and the other substituents R and R' are hydrogen.

It is preferred to use compounds of the formula II and/or III, wherein at most three substituents R or R' are different from hydrogen. Where three substituents R or R' are different from hydrogen, these can be attached to the benzene nucleus in any position.

In a further preferred embodiment, compounds of the formula II and/or III are used in which two substituents R or R' are hydrogen and the others are different from hydrogen, with the proviso that the substituents R and R' in the 4- and 5-position are not simultaneously different from hydrogen. Especially preferred are disubstituted compounds of the formulae II and/or III, wherein either the substituents R in the 5- and 6-position and the substituents R in the 3- and 4- position are hydrogen and the other substituents R and R' are different from hydrogen, or wherein the substituents R in the 4- and 7-position and the substituents R' in the 2- and 5-position are hydrogen and the other substituents R and R' are different from hydrogen.

Preferred monosubstituted compounds of the formulae II and III are those wherein the substituent R in the 5-, 6- or 7-position and the substituent R' in the 2-, 3- or 4-position are different from hydrogen.

In the preferred mono-, di- and trisubstituted compounds of the formulae II and III specified above and in the corresponding intermediates of the formula IV, substituents R and R' which are different from hydrogen have the preferred meanings assigned to them above.

It is most preferred to use compounds of the formulae II and III, wherein X is chlorine, the substituents R in the 4- and 7-position are hydrogen, the substituent R in the 5-position is hydrogen, chlorine, bromine or alkyl of 1 to 4 carbon atoms, the substituent R in the 6-position is hydrogen, alkyl or alkylthio, each containing 1 to 4 carbon atoms, or the substituents R in the 5- and 6-position together are trimethylene and the others are hydrogen, the substituents R' in the 2- and 5-position are hydrogen, the substituent R' in the 3-position is hydrogen or alkyl of 1 to 4 carbon atoms, and the substituent R' in the 4-position is chlorine, bromine, —NHCO-alkyl or —(CH$_2$)$_2$—OCO-alkyl, each containing 1 to 4 carbon atoms in the alkyl moieties, or the substituents R' in the 2- and 5-position are chlorine or bromine and the substituents R' in the 3- and 4-position are hydrogen; as well as compounds of the formulae II and III, wherein X is chlorine, the substituents R in the 4- and 7-position are alkyl of 1 to 4 carbon atoms, the substituents R' in the 2- and 5- position are hydrogen, chlorine or bromine, and the other substituents R and R' are hydrogen.

The starting materials of the formula III are known or they can be obtained by conventional methods. Some of the starting materials of the formula II are likewise known and can be obtained by the process described in German Offenlegungsschrift No. 2 804 842.

The reaction of the compounds of the formula II with a compound of the formula III is advantageously carried out in the presence of an inert organic solvent in the temperature range from about 0° to 120° C., with the preferred range being from about 20° to 70° C. Examples of suitable inert organic solvents which can be used in this reaction are: aliphatic monocarboxylic acids containing 1 to 4 carbon atoms in the alkyl moiety and alkyl esters of aliphatic monocarboxylic acids containing a total of 2 to 6 carbon atoms, such as acetic acid, propionic acid, butyric acid, and methyl, ethyl, and n-butyl formate or acetate; lower aliphatic alcohols and diols such as methanol, ethanol, n-propanol, isopropanol, n-, iso- and tert-butanol, and ethylene glycol; aliphatic ethers such as diethyl and diisopropyl ether; ethylene glycol monoalkyl and dialkyl ethers, each containing 1 to 4 carbon atoms in the alkyl moieties, such as ethylene glycol monomethyl and monoethyl ether, ethylene glycol dimethyl and diethyl ether; aliphatic ketones such as acetone and methyl ethyl ketone; chlorinated aliphatic hydrocarbons such as chloroform, 1,2-dichloroethane, 1,1,2,2-tetrachloroethane and carbon tetrachloride; N,N-dialkylamides of aliphatic monocarboxylic acids containing 1 to 3 carbon atoms in the acid moiety, such as dimethyl formamide, N,N-dimethyl acetamide and N,N-diethyl acetamide; dialkyl sulfoxides such as dimethyl and diethyl sulfoxide. The preferred solvent is anhydrous acetic acid.

The compounds of the formulae II and III are advantageously employed in equimolar amounts; however, it is also possible to use the compound of formula II in an excess of 1.1 to 5 times the molar amount.

The intermediates of the formula IV are usually obtained in the form of orange red to red crystals, which can be isolated in the customary manner and, if desired, purified, e.g. by recrystallisation. However, isolation and purification is not absolutely necessary.

The cyclisation of the intermediates of the formula IV by splitting off water is preferably carried out in the presence of a condensation agent. Examples of suitable condensation agents are polyphosphoric acid, concentrated sulfuric acid, phosphorus pentoxide or an aliphatic carboxylic anhydride such as acetic anhydride or propionic anhydride. The cyclisation in the presence of a condensation agent can be carried out with or without the addition of an inert organic solvent, advantageously in the temperature range from about 100° to 300° C., especially from about 120° to 270° C. Examples of suitable inert organic solvents are unsubstituted or chlorinated aliphatic or aromatic hydrocarbons such as 1,1,2,2-tetrachloroethane, o-dichlorobenzene, trichlorobenzenes, xylenes and nitrobenzene. It is, however, also possible to carry out the condensation by simple heating with or without the addition of a high boiling organic solvent in the temperature range from about 100° to 300° C., especially from about 150° to 270° C. Examples of suitable solvents for the condensation are trichlorobenzenes, diphenyl ether, 2-chloronaphthalene and quinoline.

It is preferred, however, first to convert the compounds of the formula IV into the acid chlorides by treatment with a chlorinating agent such as thionyl chloride, oxalyl chloride, phosgene or phosphorus pentachloride, optionally in the presence of an inert organic solvent, in the temperature range from about 0° to 100° C., especially from about 0° to 80° C. Examples of suitable inert organic solvents for the chlorination are: N,N-dialkylamides of aliphatic monocarboxylic acids containing 1 to 3 carbon atoms in the acid moiety, such as N,N-dimethyl formamide, N,N-dimethyl acetamide or N,N-diethyl acetamide; chlorinated aromatic or aliphatic hydrocarbons such as 1,2-dichloroethane, dichloromethane, chloroform or chlorobenzene. It is preferred to carry out the chlorination in dichloroethane with thionyl chloride and with the addition of a small amount of N,N-dimethyl formamide.

The cyclisation of the acid chlorides in the presence of a Friedel-Crafts catalyst (Lewis acid) can be carried out in an inert organic solvent or in the melt. Representative examples of Lewis acids which can be used are: aluminum trichloride, aluminum tribromide, zinc chloride, tin tetrachloride, boron trifluoride, iron(III) chloride, titanium tetrachloride, phosphorus trichloride, phosphoroxy chloride, antimony pentafluoride and antimony pentachloride. It is preferred to use aluminium trichloride. It is advantageous to employ an excess of the Lewis acid, e.g. about 2 to 10 times the molar amount. Examples of suitable organic solvents for the cyclisation are: chlorinated aliphatic or aromatic hydrocarbons such as dichloromethane, 1,2-dichloroethane, 1,2,2-trichloropropane, 1,1,2,2-tetrachloroethane and o-dichlorobenzene; n-pentane and n-hexane; nitromethane, nitrobenzene and carbon disulfide. The cyclisation in the melt is advantageously carried out in the presence of low melting salt mixtures, e.g. in mixtures of aluminium trichloride with inorganic or organic salts such as ammonium halides, alkaline earth metal halides and alkali metal halides, e.g. ammonium, magnesium and calcium chloride, especially sodium and potassium chloride, and also pyridinium salts, e.g. N-alkylpyridinium halides. Preferred salt mixtures for the melt cyclisation are eutectic salt mixtures, especially mixtures of aluminium trichloride and sodium chloride and/or potassium chloride. However, it is possible to use any salt mixtures, provided a sufficient lowering of the melting point is thereby attained.

It is preferred to carry out the cyclisation in the presence of a Friedel-Crafts catalyst, but in an inert organic solvent, especially dichloromethane, 1,2-dichloroethane or 1,1,2,2-tetrachloroethane, or also in the melt with the addition of sodium chloride and/or potassium chloride.

The cyclisation of the acid chlorides of the compounds of the formula IV to give compounds of the formula I is usually carried out in the temperature range from about 0° to 130° C. Depending on the nature of the solvent, the preferred temperature range for the cyclisation in the presence of an inert organic solvent is from 0° to 90° C. Usually, however, the cyclisation of the acid chlorides in the presence of an inert organic solvent can be carried out in a temperature range from about 0° to 40° C. The preferred temperature range for the cyclisation in the melt is from about 70° to 120° C.

When the reaction is complete, the compounds of the formula I can be isolated in the conventional manner. Compounds of the formula I obtained by Friedel-Crafts catalysation of the acid chlorides of intermediates of the formula IV can be isolated e.g. by pouring the reaction mixture into an icewater mixture or by addition of a dilute mineral acid such as hydrochloric acid, collecting the precipitate by filtration, and washing it with water.

The compounds of the formula I obtained by the process of this invention usually contain only minor amounts of impurities. If desired, they can be obtained in analytically pure form by recrystallisation from suitable solvents such as acetic acid, ethyl acetate, cellosolve, ethylene glycol dimethyl or diethyl ether, acetone, methanol or ethanol, or by suspending them in one of these solvents and then collecting them by filtration.

The compounds of the formula I are obtained in the form of red to dark violet crystals and some of them are known. It is also possible, however, to obtain symmetrical thioindigo compounds of the formula I with heretofore unknown combinations of substituents by the process of this invention. As already mentioned, the compounds of the formula I can be used, inter alia, in known manner as vat, disperse, melt spinning and pigment dyes [cf. for example German Offenlegungsschrift Nos. 2 401 981 and 2 520 196, and U.S. patent specifications Nos. 2,882,277 and 3,793,341].

EXAMPLES 1–15: Production of compounds of the formula IV 25.5 g (0.1 mole) of 2-chlorocarboxymethylene-5-methyl-[2H]-benzothiophen-3-one (obtained in accordance with German Offenlegungsschrift No. 2 804 842) are suspended at 20° C. in 300 ml of anhydrous acetic acid and to this suspension are added 11 g (0.1 mole) of thiophenol. The reaction mixture is then heated for 1½ hours to 50° C. After cooling, the orange red precipitate is collected by filtration, washed with anhydrous acetic acid and dried at 60° C./13000 Pa, affording 28 g (85.4% of theory) of 2-thiophenyl-carboxymethylene-4-methylbenzothiophen-3-one in the form of orange red crystals with a melting point of 164°–167° C. (decompos.).

IR spectrum (KBr; w=weak, m=medium, s=strong): $3115^m$, $1750^s$, $1670^s$, $1610^m$, $1545^s$, $1470^s$, $1285^s$, $1220^s$, $1165^m$, $1100^s$, $1020^m$, $1005^m$, $826^m$, $775^s$, $745^s$.

$R_f$ (silica gel/eluant (v:v) toluene/acetic acid 70:30): 0.51

Elemental analysis for $C_{17}H_{12}S_2O_3$: calculated C 62.18%, H 3.69%, S 19.53%, found C 62.2%, H 3.7%, S 19.5%.

Table I lists further compounds of the formula IV which were obtained by the procedure described above.

EXAMPLES 16–30: Production of compounds of the formula I from compounds of the formula IV according to Examples 1–15

11.5 g (0.035 mole) of 2-thiophenylcarboxymethylene-5-methylbenzothiophen-3-one are suspended in 100 ml of 1,2-dichloroethane. To this suspension are added 12.6 g (0.015 mole) of thionyl chloride and 2 ml of N,N-dimethyl formamide, and the mixtue is heated for 4 hours to 60° C. The dark red solution is then concentrated and the precipitated orange powder is added to 85 g (0.36 mole) of aluminium trichloride in 85 ml of 1,2-dichloroethane, while keeping the temperature at 20° C. with an external ice bath. After stirring for 15 hours at 20°–25° C., the black suspension is poured on ice and stirred for 20 minutes. The red crystals obtained are collected by filtration after addition of 50 ml of ethyl acetate. These crystals are washed with 50 ml of ethyl acetate and dried at 60° C./13000 Pa, affording 10.4 g (96% of theory) of 5-methylthioindigo in the form of red crystals with a melting point of >250° C.

IR spectrum (KBr; w=weak, m=medium, s=strong): $1655^s$, $1600^m$, $1475^m$, $1450^m$, $1385^s$, $1225^m$, $1175^m$, $1080^s$, $1060^w$, $900^s$, $815^m$, $775^m$, $745^s$.

Elemental analysis for $C_{17}H_{10}O_2S_2$:
calculated C 65.79%, H 3.25%, S 20.66%, O 10.31%, found C 65.65%, H 3.26%, S 20.13%, O 10.62%.

$R_f$ [silica gel/eluant: toluene/acetic acid (v:v)=70:30]: 0.78

Table II lists further compounds of the formula I which were obtained from the corresponding compounds of the formula IV by the procedure described above.

TABLE I

Compound (II) / Compound (III)

| Example | $R_1$ | $R_2$ | $R_3$ | $R_4$ | $R_5$ | $R_6$ | $R_7$ | $R_8$ | $R_f$ [silica gel/eluant (v:v) toluene/glacial acetic acid 70:30] |
|---|---|---|---|---|---|---|---|---|---|
| 2 | H | Cl | H | H | H | Br | H | H | 0.63 |
| 3 | H | Cl | H | H | Cl | H | H | Cl | 0.52 |
| 4 | H | Br | $CH_3$ | H | Cl | H | H | Cl | 0.56 |
| 5 | H | Cl | H | H | H | $-NHCOCH_3$ | H | H | 0.17 |
| 6 | H | H | $SCH_3$ | H | H | Cl | H | H | 0.55 |
| 7 | H | Cl | H | H | H | Br | $CH_3$ | H | 0.53 |
| 8 | $CH_3$ | H | H | $CH_3$ | Cl | H | H | Cl | 0.44 |
| 9 | H | $CH_3$ | H | H | H | Br | $CH_3$ | H | 0.58 |
| 10 | H | $-CH_2CH_2CH_2-$ | | H | H | Cl | H | H | 0.61 |
| 11 | H | $n-C_4H_9$ | H | H | H | Cl | H | H | 0.58 |
| 12 | $CH_3$ | H | H | $CH_3$ | H | H | H | H | 0.59 |
| 13 | H | Br | $CH_3$ | H | Cl | H | H | Cl | 0.48 |
| 14 | H | $CH_3$ | H | H | H | $-(CH_2)_2OCOCH_3$ | H | H | 0.48 |
| 15 | H | $n-C_4H_9$ | H | H | Cl | H | H | Cl | 0.56 |

TABLE II

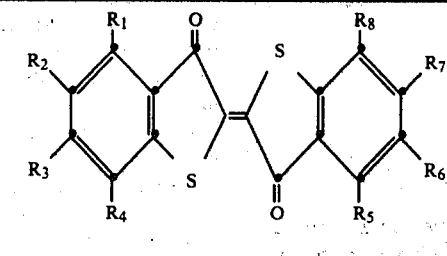

| Example | Starting material according to | R₁ | R₂ | R₃ | R₄ | R₅ | R₆ | R₇ | R₈ | R_f [silica gel/ eluant (V:V) toluene/glacial acetic acid 70:30] | Colour/ substrate |
| --- | --- | --- | --- | --- | --- | --- | --- | --- | --- | --- | --- |
| 17 | Ex. 2 | H | Cl | H | H | H | Br | H | H | reluctantly soluble | violet pink/PES |
| 18 | Ex. 3 | H | Cl | H | H | Cl | H | H | Cl | 0.88 | bluish red/PVC |
| 19 | Ex. 4 | H | Br | CH₃ | H | Cl | H | H | Cl | 0.88 | bluish red/PVC |
| 20 | Ex. 5 | H | Cl | H | H | H | —NHCOCH₃ | H | H | 0.44 | bluish violet/PES |
| 21 | Ex. 6 | H | H | SCH₃ | H | H | Cl | H | H | 0.89 | violet/PES |
| 22 | Ex. 7 | H | Cl | H | H | H | Br | CH₃ | H | 0.88 | violet/PVC |
| 23 | Ex. 8 | CH₃ | H | H | CH₃ | Cl | H | H | Cl | 0.86 | violet/PES |
| 24 | Ex. 9 | H | CH₃ | H | H | H | Br | CH₃ | H | 0.88 | violet/PES |
| 25 | Ex. 10 | H | —CH₂CH₂CH₂— | | H | H | Cl | H | H | 0.85 | violet/PES |
| 26 | Ex. 11 | H | n-C₄H₉ | H | H | H | Cl | H | H | 0.90 | violet/PES |
| 27 | Ex. 12 | CH₃ | H | H | CH₃ | H | H | H | H | 0.83 | red/PES |
| 28 | Ex. 13 | H | Br | CH₃ | H | Cl | H | H | Cl | 0.89 | reddish brown/PES |
| 29 | Ex. 14 | H | CH₃ | H | H | H | —(CH₂)₂OCOCH₃ | H | H | 0.72 | red/PES |
| 30 | Ex. 15 | H | n-C₄H₉ | H | H | Cl | H | H | Cl | 0.91 | pink/PES |

PES = polyester fibres coloured in accordance with Application Example A
PVC = polyvinyl chloride coloured in accordance with Application Example B

APPLICATION EXAMPLES

EXAMPLE A

A non-delustred polyethylene terephthalate granulate suitable for fibre manufacture is shaken for 15 minutes on a mechanical shaker together with 1% by weight of the 5-methylthioindigo compound obtained in Example 16. The coloured granules are then spun in a melt spinning machine (285° C.±3° C., sojourn time in the spinning machine about 5 minutes) to filaments, which are stretched and wound on a draw twister. The brilliant claret colouration obtained is distinguished in particular by excellent lightfastness.

EXAMPLE B 65 parts by weight of stabilised polyvinyl chloride, 35 parts by weight of dioctyl phthalate and 0.2 part by weight of the pigment dye obtained in Example 18 are stirred together and then rolled for 7 minutes at 140° C. on a two-roll calender. A bluish red colouration of good fastness to light and migration is obtained.

EXAMPLE C 100 parts by weight of polyethylene terephthalate granules and 0.2 part by weight of the pigment dye obtained in Example 17 are thoroughly mixed in a mixing drum and then dried for about 24 hours at 100° C. in vacuo at 135×10⁻³Pa. The coloured granules are extruded at about 280° C. to a ribbon in a single screw extruder. A strong violet colouration of excellent lightfastness properties is obtained.

What is claimed is:

1. A process for the production of the compound of the formula I

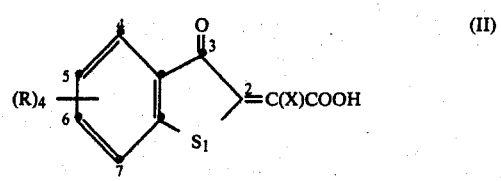

wherein two substituents R or R' are hydrogen or alkyl of 1 to 12 carbon atoms, one R or R' is hydrogen, a halogen atom or alkyl of 1 to 12 carbon atoms, and one R or R' is hydrogen, a halogen atom, alkyl, alkoxy, alkylthio, alkoxyalkyl, alkanoyloxyalkyl or alkylcarbamoyl, each containing 1 to 12 carbon atoms in the alkyl and alkoxy moieties and 2 to 13 carbon atoms in the alkanoyl moieties, or two adjacent substituents R or R' together are trimethylene or tetramethylene and the other substituents R are hydrogen, with the proviso that at least one substituent R is different from a substituent R', which process comprises reacting a compound of the formula II $$(R)_4 \begin{array}{c} \phantom{X} \\ \phantom{X} \end{array} \!\!\!\! \begin{array}{c} O \\ \| \\ \end{array}\!\!\!\! \begin{array}{c} \\ \\ S_1 \end{array} = C(X)COOH \quad (II)$$

with a compound of the formula III

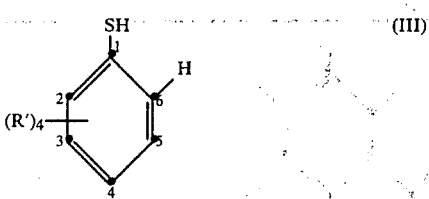

in the presence of an inert organic solvent at a temperature between about 0° and 120° C. to form a compound of the formula IV

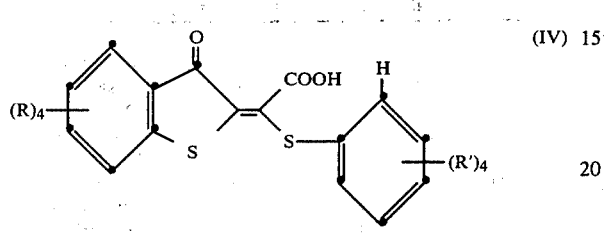

in which formulae II, III and IV above X is chlorine, bromine or fluorine and R and R' are as defined for formula I; and cyclising said compound of the formula IV either directly by splitting off water, optionally in the presence of a condensation agent, with or without the addition of an inert organic solvent at a temperature between about 100° and 300° C., or by heating, with or without the addition of a high-boiling organic solvent, at a temperature between about 100° and 300° C., to give a compound of the formula I, or converting said compound of the formula IV into the corresponding acid chloride by treating it with a chlorinating agent, optionally in the presence of an inert organic solvent, at a temperature between about 0° and 100° C., and cyclising this latter, in the presence of a Friedel-Crafts catalyst in an inert organic solvent or in a melt at a temperature between about 0° and 130° C., to give a compound of the formula I.

2. A process according to claim 1 which comprises the use of a compound of the formula II and/or III, wherein two substituents R or R' are hydrogen or alkyl of 1 to 4 carbon atoms, one R or R' is hydrogen, chlorine, bromine or alkyl of 1 to 4 carbon atoms, and one R or R' is hydrogen, chlorine, bromine, alkyl, alkoxy, alkylthio, —(CH$_2$)$_2$—O-alkyl,

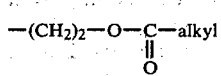

or —NHCO-alkyl, each containing 1 to 4 carbon atoms in the alkyl moieties, and X is chlorine.

3. A process according to claim 1 which comprises the use of a compound of the formula II and/or III, wherein two substituents R or R' are hydrogen and the others are different from hydrogen, with the proviso that the substituents R and R' in the 4- and 5-position are not simultaneously different from hydrogen.

4. A process according to claim 1 which comprises the use of a compound of the formula II and/or III, wherein either the substituents R in the 5- and 6-position and the substituents R' in the 3- and 4-position are hydrogen and the other substituents R and R' are different from hydrogen, or wherein the substituents R in the 4- and 7-position and the substituents R' in the 2- and 5-position are hydrogen and the other substituents R and R' are different from hydrogen.

5. A process according to claim 1 which comprises the use of a compound of the formula II or III, wherein the substituent R in the 5-, 6- or 7-position or the substituent R' in the 2-, 3- or 4-position is different from hydrogen.

6. A process according to claim 1 which comprises the use of a compound of the formula II and III, wherein X is chlorine, the substituents R in the 4- and 7-position are hydrogen, the substituent R in the 5-position is hydrogen, chlorine, bromine or alkyl of 1 to 4 carbon atoms, the substituent R in the 6-position is hydrogen, alkyl or alkylthio, each containing 1 to 4 carbon atoms, or the substituents R in the 5- and 6-position together are trimethylene and the others are hydrogen, the substituents R' in the 2- and 5-position are hydrogen, the substituent R' in the 3-position is hydrogen or alkyl of 1 to 4 carbon atoms, and the substituent R' in the 4-position is chlorine, bromine, —NHCO-alkyl or —(CH$_2$)$_2$—OCO-alkyl, each containing 1 to 4 carbon atoms in the alkyl moieties, or the substituents R' in the 2- and 5-position are chlorine or bromine and the substituents R' i the 3- and 4-position are hydrogen.

7. A process according to claim 1 which comprises the use of a compound of the formula II and III, wherein X is chlorine, the substituents R in the 4- and 7-position are alkyl of 1 to 4 carbon atoms, the substituents R' in the 2- and 5-position are hydrogen, chlorine or bromine, and the other substituents R and R' are hydrogen.

8. A process according to claim 1, wherein the cyclisation of the acid chloride of a compound of the formula IV is carried out in the presence of an inert organic solvent in the temperature range from about 0° to 90° C., or in the melt, with the addition of sodium and/or potassium chloride, in the temperature range from about 70° to 120° C.

9. A process according to claim 1, wherein aluminium trichloride is used as Friedel-Crafts catalyst for the cyclisation of the acid chloride of a compound of the formula IV.

* * * * *